United States Patent [19]

Thompson et al.

[11] 4,340,062
[45] Jul. 20, 1982

[54] BODY STIMULATOR HAVING SELECTABLE STIMULATION ENERGY LEVELS

[75] Inventors: David L. Thompson, Fridley; Ray S. McDonald, St. Paul; Yan S. Lee, Plymouth, all of Minn.; Marc T. Stein, Tempe, Ariz.

[73] Assignee: Medtronic, Inc., Minneapolis, Minn.

[21] Appl. No.: 182,597

[22] Filed: Aug. 29, 1980

Related U.S. Application Data

[63] Continuation of Ser. No. 957,827; Nov. 6, 1978, abandoned.

[51] Int. Cl.³ .............................................. A61N 1/36
[52] U.S. Cl. .............................................. 128/419 PG
[58] Field of Search ................................ 128/419 PG

[56] References Cited

U.S. PATENT DOCUMENTS

| | | | |
|---|---|---|---|
| 3,717,152 | 2/1973 | Vandenberg | 128/419 PG |
| 3,777,762 | 12/1973 | Nielsen | 128/419 PG |
| 3,845,773 | 11/1974 | Fontaine et al. | 128/419 PG |
| 3,920,024 | 11/1975 | Bowers | 128/419 PG |

Primary Examiner—William E. Kamm
Attorney, Agent, or Firm—Schroeder, Siegfried, Vidas, Steffey & Arrett

[57] ABSTRACT

A body implantable stimulator for providing stimulation signals having selectable energy levels. The stimulator provides a series of one of a predetermined plurality of independent output initiate signals and responds to those signals to provide stimulation signals having an amplitude, duration and repetition rate established by the series of output initiate signals that is provided.

10 Claims, 2 Drawing Figures

BODY STIMULATOR HAVING SELECTABLE STIMULATION ENERGY LEVELS

This is a continuation, of application Ser. No. 957,827, filed Nov. 6, 1978 now abandoned.

DESCRIPTION

BACKGROUND OF PRIOR ART

Body implantable cardiac stimulators or pacemakers are known to the prior art. An early pacemaker is disclosed by Greatbatch in U.S. Pat. No. 3,057,356, entitled "Medical Cardiac Pacemaker", which issued in 1962. This device included a relaxation oscillator that generated electrical pulses at a fixed rate. The pulses were applied to the heart to cause the heart to contract each time a pulse occurred.

Since 1962, the pacemaker has been continuously evolving. This evolution is outlined in concurrently filed co-pending application Ser. No. 957,962, now U.S. Pat. No. 4,250,883, filed in the name of David L. Thompson for Digital Cardiac Pacemaker, which is co-owned with the present invention and which is hereby incorporated by reference. As noted in the incorporated specification, pacing technology has lagged behind conventional state of the art electronic technology in its utilization of digital electronic circuits. One reason for this has been the high energy required to operate digital electronic circuits. Energy requirements are a major concern in pacemaker design. However, with the continuing advances of electronic technology, digital electronic circuits are increasingly feasible within the context of commercial pacemaker units.

The accuracy and reliability of digital electronic circuits are factors that encourage their use within the pacemaker context. The facility with which they can be programmed and reprogrammed to alter one or more operating parameters further enhances their utility. For example, pacemakers have been disclosed which respond to magnetic and/or radio frequency signals to alter an operating parameter. Pulse rate and pulse width may be programmed in this manner. In addition, pacemakers have been constructed which are inhibited in the presence of certain signals. A more detailed outline of prior art programmable pacemakers is contained in the incorporated specification. It should be noted that, as indicated in the incorporated specification, no known prior art pacemaker is capable of having more than two parameters, features or tests programmed on command.

The implementation of digital electronic circuitry within the pacemaker context provides the opportunity to program or reprogram one or several operating parameters, on command, via externally generated signals. For example, pulse rate, pulse width and pulse amplitude can be externally established at one of any number of combinations. In addition, the refractory period may be established and altered. Further, digital circuitry can be programmed on a temporary or permanent basis, as desired. Of course, other operating parameters or characteristics can also be externally programmable.

Clearly then, a pacemaker utilizing digital electronic circuitry would have a more universal application by allowing the pacemaker to be programmed to fit the needs of a particular application as opposed to being manufactured for limited applications. In addition, such a unit can be instructed to give an external indication of its program status, particularly in instances where that status is not directly observable. However, even with the implementation of digital circuitry, certain analog circuitry is necessary to generate and/or transmit various control signals and to respond to the digital circuitry to effect its programming.

BRIEF SUMMARY OF THE INVENTION

The present invention provides analog circuitry intended for cooperation with the digital circuitry disclosed in the incorporated specification to assist in the performance of the pacemaking function. Among the analog circuit functions necessary within the context of the digital circuitry of the incorporated specification, are the demodulation of the programming signal, a detection of heart activity during operation in a demand mode and provision of clock pulses. Additionally, analog circuitry is employed to give an indication of battery status and to impose an upper rate limit on the stimulation initiating signals generated by the digital circuit. The digital circuitry of the incorporated specification provides a signal to control the sensitivity of the sense amplifier and a signal to establish a refractory period within the sense amplifier. The output analog circuit is controlled by the digital circuit to speed up the recharging of a capacitor in the output circuit, to establish the magnitude of the output pulses and to impose an upper rate limit on the output stimulation pulses. As detailed in the incorporated specification, one of the clock pulse generators is enabled by a signal from the digital circuit.

Within the context of cooperating analog and digital circuitry for the generation and application of stimulating pulses, the present invention is directed to an output circuit for the provision of stimulation signals, the circuit being responsive to output initiate signals from the digital circuitry to establish the amplitude, duration and repetition rate of the stimulation signals while providing a fast recharge of the output capacitor following a stimulation signal and establishing an upper rate limit for the generation of output initiate signals by the digital circuitry and stimulation signals by the output circuit. In addition, the output circuit is responsive to a signal from the digital circuitry to establish an independent upper rate limit on the generation of stimulation signals.

In accordance with its programming, the digital circuitry generates an output initiate signals the form of a series of SINGLE or DOUBLE signals. Each output initiate signal results in the provision of a stimulation signal by the output circuit, the repetition rate and duration of the stimulation signal being established by the repetition rate and duration of the output initiate signal, respectively. The amplitude of the stimulation signal is dependent on the series output initiate signal generated by the digital circuitry. For example, the generation of a DOUBLE signal results in a stimulation signal having an amplitude approximately twice the supply voltage. A SINGLE initiate signal results in a stimulation signal having an amplitude approximately equal to the supply voltage. Thus, the output circuit of the present invention will provide stimulation signals having an amplitude established by the output initiate signals generated by the digital circuitry. The ability to alter the stimulation signal amplitude, duration and repetition rate provides great flexibility in establishing the operating parameters during normal operation as well as during testing of the stimulator and its interaction with the body.

During the delivery of a stimulation signal, the output capacitor is partially discharged and recharges during the interval between stimulation signals. At higher rates, particularly with long duration signals, the capacitor may not fully charge during that interval. This potential problem could be accommodated by reducing the time constant of the charge path of the output capacitor. However, in the context of a demand cardiac pacemaker it is desireable to have a high impedance in that path in that a high input impedance, as viewed from the heart, aids in sensing R waves. However, this higher impedance increases the time constant and, thus, the time of recharge. The sense amplifier of a demand cardiac pacemaker senses this activity and, thus, it would be desireable to speed up the recharge of the output capacitor to speed up the recovery of the sense amplifier. The output circuit of the present invention provides a high input impedance, as viewed from the body tissue being stimulated, while increasing the charge rate of the output capacitor for a predetermined period following each stimulation pulse under the control of a RECHARGE signal generated by the digital circuitry.

As indicated above, the output circuit of the present invention provides a stimulation signal in accordance with an output initiate signal generated by the digital circuitry. The repetition rate of the stimulation signal is dependent on the repetition rate of the output initiate signal. Therefore, in the event that the digital circuitry should fail such that output initiate signals are generated at a rate higher than desireable, the stimulation signal providing portion of the output circuit of the present invention would respond to those initiate signals and provide stimulation signals at a repetition rate higher than desireable. The output circuit of the present invention provides a rate limit circuit which prevents the response of the output circuit to the output initiate signals for a predetermined time after each output initiate signal thereby providing an upper rate limit to the stimulation signals. In addition, a RATE LIMIT signal is applied to the digital circuitry during that same period to prevent the generation of output initiate signals. As described in the incorporated specification, the digital circuitry may be programmed to provide a rate limit disable signal to the output circuit, the output circuit responding to the rate limit disable signal from the digital circuitry to prevent the provision of the RATE LIMIT signal and to allow the output circuit to respond to all output initiate signals.

DETAILED DESCRIPTION OF THE INVENTION

Figure 1:
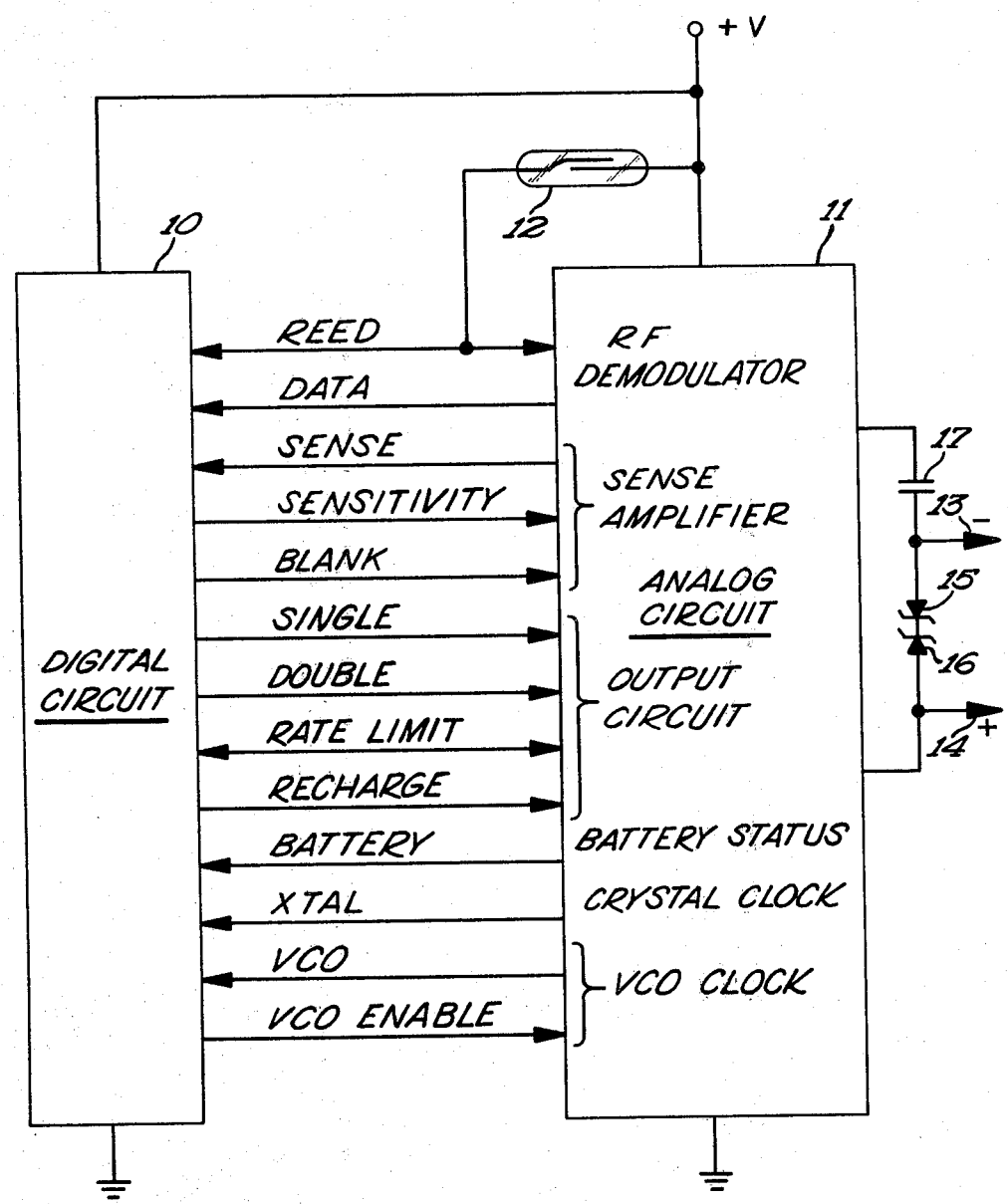
FIG. 1 shows the interconnection and cooperation between the digital circuit of the incorporated specification and a cooperating analog circuit of which the present invention is a part.

Referring now to FIG. 1 there is shown a block diagram illustrating the interconnections between Digital Circuitry 10 (as disclosed in the incorporated specification) and Analog Circuitry 11 (of which the present invention is a part). Both the Digital Circuit 10 and Analog Circuit 11 are connected between a source of positive potential +V and a reference potential, such as ground. The source of positive potential may be a battery such as the conventional lithium iodide battery which generates approximately 2.8 volts.

The Analog Circuit 11 consists of various distinct electrical systems which may be referred to functionally as an RF Demodulator, a Sense Amplifier, an Output Circuit, a Battery Monitor and Status Indicator, a Crystal Clock and a Voltage Controlled Oscillator Clock. The Digital Circuit 10 includes all of the digital logic necessary to cause a programming change, memory to store the digital code manifesting the desired values for the program parameters and digital timing means for causing a stimulation pulse to be generated in the programmed manner. The signals applied between the Digital Circuit 10 and Analog Circuit 11 are REED, DATA, SENSE, SENSITIVITY, BLANK, SINGLE, DOUBLE, RATE LIMIT, RECHARGE, BATTERY, XTAL, VCO and VCO ENABLE.

A magnetically actuated reed relay switch 12 is connected between the source of positive potential +V and both the Digital Circuit 10 and the RF Demodulator of Analog Circuit 11. Reed switch 12 is normally open and is closed as by placing a magnet in close proximity thereto. When closed, a +V, or logic "1", REED signal is applied to both the Digital Circuit 10 and Analog Circuit 11. On removal of the magnet, the reed switch 12 opens and a ground, or logic "0", signal is applied to the Digital Circuit 10 and Analog Circuit 11. The RF Demodulator is enabled by a +V REED signal produced by a closing of the reed switch 12 to provide a DATA signal to the digital circuit 10. The DATA signal (the Digital Circuit 10 programming signal) is a pulse signal going from logic "0" to logic "1", as described in the incorporated specification, which is representative of pulse bursts generated externally.

The Sense Amplifier portion of the analog circuit 11 provides a SENSE signal each time natural heart activity is detected to restart the timing cycle of the Digital Circuit 10, when operating in a demand mode. A SENSITIVITY signal is provided by the Digital Circuit 10 in accordance with its programming to establish the detection level of the Sense Amplifier. A BLANK signal is generated by the Digital Circuit 10 and applied to the Sense Amplifier portion of the Analog Circuit 11 to establish the refractory period of the Sense Amplifier and to allow the components within the Sense Amplifier to reset themselves.

The Output Circuit of analog circuit 11 includes output terminals 13 and 14 which are adapted for connection to a conventional lead, in a known manner. The output terminal 14 may be connected to a metal casing housing the pacemaker unit or a plate forming a part of the casing in a unipolar lead system or it may be connected to a second lead in a bipolar lead system, depending on the type of lead system employed. Output terminal 13 is coupled through a capacitor 14 to the analog Output Circuit and to the heart (not shown). In addition, a pair of Zener diodes 15 and 16 have their anodes coupled together and their cathodes coupled to output terminals 13 and 14, respectively. Diodes 15 and 16 function in a conventional manner to prevent damage to the pacemaker circuitry in the presence of large extraneous signals such as are caused by electrocautery. The Output Circuit of Analog Circuit 11 includes elements responsive to a series of SINGLE or DOUBLE signal from Digital Circuit 10 to control the amplitude of output signals applied across output terminals 13 and 14. A RECHARGE signal from Digital Circuit 10 speeds up the recharging of output capacitor 14 while the Output Circuit of Analog Circuit 11 provides a RATE LIMIT signal to Digital Circuit 10 to provide an upper limit to the rate at which stimulation initiating signals are generated. Digital circuit 10 also provides a rate limit disable signal to the Output Circuit of Analog Circuit 11 to eliminate the upper limit to the rate at which stimulation pulses may be applied by the Output Circuit.

In addition to the above, Analog Circuit 11 includes circuitry which monitors the status of the battery to provide an indication of that status in the form of the signal BATTERY. Also, clock pulses are provided to the Digital Circuit 10 in the form of signals XTAL and VCO. Within the context of the Digital Circuit of the incorporated specification, the XTAL signal is a generally square wave pulse signal occuring at a frequency of 32,768 Hz and the VCO signal is a square wave pulse signal having a preset frequency whenever +V is equal to 2.8 volts. As +V decreases with time, as the battery depletes, the frequency of the VCO signal will also decrease, in known manner. The VCO signal is used in the timing circuitry of Digital Circuit 10 to establish the exact width of stimulating pulse. In order to maintain a constant energy of this pulse, it is necessary that the pulse increase in width as +V decreases. The VCO clock pulse generator is enabled only during the time the stimulating pulse is to be provided and is enabled by the signal VCO ENABLE.

Figure 2:
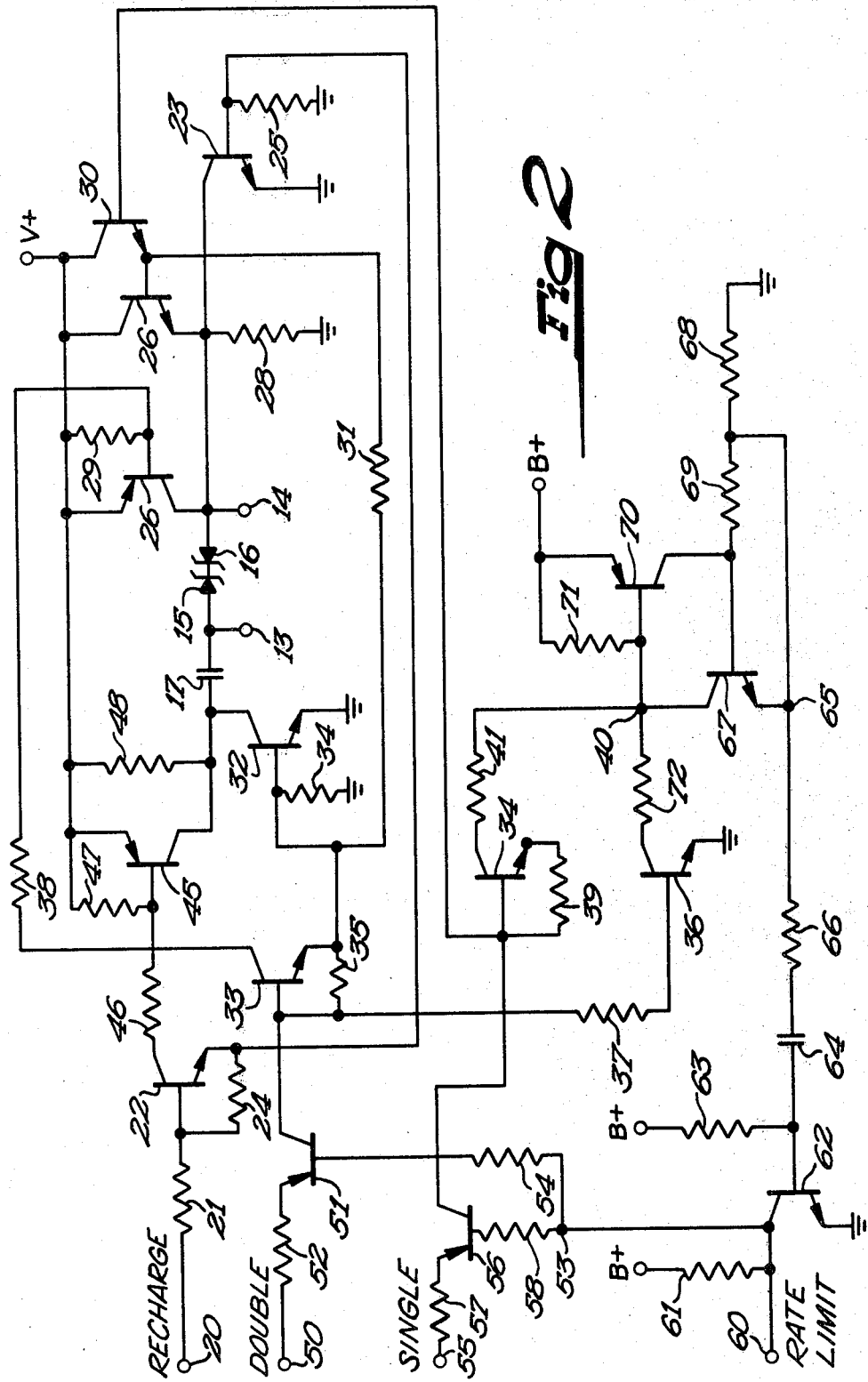
FIG. 2 illustrates the operation of an output circuit forming a part of the analog circuitry of FIG. 1.

Referring now to FIG. 2, there is shown a preferred embodiment of the output circuit of the present invention with elements 13–17 of FIG. 2 being those of like reference numeral illustrated in FIG. 1. A terminal 20 is adapted to receive the RECHARGE signal from digital circuit 10 of FIG. 1 and is connected to a resistor 21. Resistor 21 is connected to the base of a transistor 22 and to the emitter of transistor 22 and the base of transistor 23 via resistor 24. The base of transistor 23 is connected to ground via resistor 25 while its emitter is connected to ground and its collector is connected to terminal 14 and to the collector of transistor 26 and the emitter of transistor 27. The emitter of transistor 27 is connected to ground via resistor 28 while its collector and the emitter of transistor 26 are connected to a positive potential V+. A resistor 29 connects the base of transistor 26 to V+. A transistor 30 has its collector connected V+ while its emitter is connected to the base of transistor 27 and to a resistor 31. The resistor 31 is connected to the base of a transistor 32, the emitter of transistor 33 and the emitter of a transistor 34. The base of transistor 32 is connected to ground via resistor 34 while its emitter is connected to ground and its collector is connected to capacitor 17. The emitter of transistor 33 is connected to its base via resistor 35 and to the base of a transistor 36 via resistor 37. A resistor 38 connects the collector of transistor 33 to the base of transistor 26. The emitter of transistor 34 is connected via resistor 39 to its base and to the base of transistor 30 while its collector is connected to a junction 40 via resistor 41.

The collector of transistor 22 is connected to the base of a transistor 45 via a resistor 46, the base and emitter of transistor 45 being connected via resistor 47. A resistor 48 interconnects the emitter and collector of transistor 45, the collector of transistor 45 being connected to the capacitor 17.

A terminal 50 is adapted for connection to receive a DOUBLE signal from digital circuit 10 and is connected to the emitter of a transistor 51 via a resistor 52. The collector of transistor 51 is connected to the base of transistor 33 while its base is connected to a junction 53 via resistor 54. A terminal 55 is adapted for connection to receive the SINGLE signal from the digital circuit 10 and is connected to the emitter of a transistor 56 via resistor 57. The collector of transistor 56 is connected to the base of transistor 34 while its base is connected to junction 53 via resistor 57. A terminal 60 is adapted for connection to receive the RATE LIMIT signal from digital circuit 10 and is connected to a positive potential B+ via resistor 61 and to the collector of a transistor 62 and the junction 53. The emitter of transistor 62 is connected to ground and its base is connected to B+ via a resistor 63 and to a capacitor 64. The capacitor 64 is connected to a junction 65 via a resistor 66, the junction 65 being connected to the emitter of a transistor 67 to ground via a resistor 68 and to the base of transistor 67 via a resistor 69. The base of transistor 67 is connected to the collector of a transistor 70 while its collector is connected to the junction 40. The emitter of transistor 70 is connected to B+ and to its base and junction 40 via a resistor 71. The collector of transistor 36 is connected to junction 40 via resistor 72. As described above, V+ is a source of positive potential. B+ indicates a positive potential source that is filtered to prevent the ripple caused by a stimulation pulse from turning on the rate limit circuitry in the middle of a stimulation pulse and thus cause a loss of a part of the stimulation pulse.

As outlined above, a DOUBLE signal appearing at terminal 50 will result in a stimulation signal at terminals 13 and 14 approximately twice the potential of V+. The DOUBLE signal is a positive pulse having a duration that is essentially the duration of the desired stimulation pulse. This pulse turns on transistor 51 resulting in the turn on of transistor 33. The turn on of transistor 33 causes transistors 26 and 32 to saturate. Assuming that capacitor 17 had charged to V+, the turn on of transistor 32 connects the left or positive side of capacitor 17 to ground driving its right side and terminal 13 negative. The turn on of transistor 26 connects terminal 14 to V+ and, accordingly, the voltage across terminal 13 and 14 is $V+ -(-V+) = 2V+$. In practice, of course, saturation losses will result in a slightly lower voltage applied across the terminals 13 and 14.

The SINGLE signal applied to terminal 55 is a positive pulse having a duration essentially that of the desired stimulation pulse. This signal turns on transistor 56 which turns on transistors 34 and 30. The turn on of transistor 34 again causes transistor 32 to saturate again forcing the terminal 13 negative. Transistor 30 turns on transistor 27. However, the emitter of transistor 27 is clamped at ground potential due to the fact that the base emitter voltage of transistor 34 plus that of transistor 32 must equal the base emitter voltage of transistor 30 plus that of transistor 27. Thus, terminal 14 is maintained at ground potential and approximately the negative of V+ is applied across the terminals 13 and 14. Again, of course, the saturation losses in transistor 32 reduces the potential across the terminals 13 and 14 by a small amount.

During the stimulation pulse resulting from the SINGLE output initiate signal, transistor 32 is saturated while transistor 27 is in its linear range. Thus, at the end of the SINGLE signal, transistor 27 would turn off faster than transistor 32. However, terminal 13 would still be negative when transistor 27 turns off resulting in a path for current flow through the body tissue connected between terminals 13 and 14 and resistor 28 producing a negative spike on the collector of transistor 23. Resistor 31 eliminates this spike by providing a low impedance path for the base of transistor 32 which allows transistor 32 and 27 to turn off simultaneously.

During the delivery of a stimulation signal, capacitor 17 is partially discharged—typically on the order of 0.5 volt. A short time after the stimulation signal has ended the digital circuitry 10 provides a RECHARGE signal in the form of a positive pulse applied to terminal 20. The RECHARGE signal has a pulse width of approximately 10 milliseconds and turns on transistor 22. The turn on of transistor 22 causes transistors 45 and 23 to saturate allowing capacitor 17 to charge quickly through transistor 23, the body tissue connected between terminals 13 and 14 and transistor 45. During this fast recharge interval, (the duration of the RECHARGE Signal) capacitor 17 charges to approximately V+ less saturation losses in transistors 23 and 45. Those transistors may be selected to minimize the saturation losses and thus maximize the charge on capacitor 17. Resistors 28 and 48 allow the continued charging of capacitor 17 after the fast recharge interval until the next output pulse is initiated. Thus, the output circuit of the present invention provides means for increasing the charge rate of the output capacitor by providing first and second charge paths for the capacitor, one charge path being selectively conductive and of a lower impedance than the other path. In the illustrated embodiment, transistors 23 and 45 provide shunts across resistances within a normal capacitor charge path thereby reducing the impedance and time constant of the charge path during the time that the RECHARGE signal is applied to the terminal 20. A high impedance is maintained at all other times as an aid in sensing R waves.

Transistor 62 is normally saturated resulting in a "zero" or ground condition at terminal 60. A positive signal applied to the terminal 60 disables the transistors 51 and 56 and prevents them from turning on in response to an output initiate signal. In essence, such a condition blocks the output initiate signals. Within the Output Circuit of the present invention, a positive signal on terminal 60 is obtained, via resistor 61, when transistor 62 is "off". Turn on of transistor 62 causes its collector to go to ground potential thus enabling transistors 51 and 56 and, accordingly, the output circuit of FIG. 2. The signal at terminal 60 resulting from the turn on and turn off of transistor 62 may also be applied as the RATE LIMIT signal to the digital circuit 10 to enable and disable the generation of output initiate signals. Accordingly, the turn off of transistor 62 may be employed as a disable signal in the digital circuit 10 to prevent the generation of output initiate signals thereby providing an additional upper rate limit.

The appearance of a SINGLE or DOUBLE output initiate signal results in a signal at junction 40 and a turn on of transistor 67 and 70. For example, a DOUBLE signal at terminal 50 will turn on transistor 51 resulting in a turn on of transistor 36 and a signal at junction 40. A SINGLE signal at terminal 55 will turn on transistor 56 resulting in a turn on of transistor 34 and a signal at junction 40. In either event, a signal at junction 40 results in the turn on of transistor 67 and 70 which are connected in an SCR arrangement. Once the circuit of transistors 67 and 70 is triggered, capacitor 64 will charge and transistors 67 and 70 will remain on until capacitor 64 is charged and the SINGLE or DOUBLE output initiate signal terminates. Thus, the on time of transistors 67 and 70 is established by the duration of the output initiate signal with the change time of capacitor 64 setting a minimum on time. On termination of the SINGLE or DOUBLE output initiate signal, with capacitor 64 charged, the transistors 67 and 70 will turn off returning the right side of capacitor 64 to ground via resistors 66 and 68. Since the voltage across capacitor 64 cannot change instantaneously, the base of transistor 62 is driven negative cutting it off and causing its collector to go positive. This positive signal at the collector of transistor 62 disables the transistors 51 and 56 and may be employed as a RATE LIMIT disable signal within the analog circuit 10. With transistors 67 and 70 off, capacitor 64 charges toward B+ through resistors 63, 66 and 68 until the base of transistor 62 is forward biased. At that time, transistor 62 turns on putting a zero condition at terminal 60, again enabling transistors 51 and 56. The maximum output stimulation rate is thus limited by the time that transistor 62 is off, that time being established by the time constant of the circuitry including capacitor 64 and resistors 63, 66 and 68 and being selectable at any desired rate, in known manner. It should be noted that the transistors 67 and 70 stay on for at least the duration of a SINGLE or DOUBLE output initiate signal which prevents the turn off of transistor 62 during those signals and, thus, prevents the disruption of a stimulation signal.

As described above, the present invention provides an output circuit within the context of cooperating analog and digital circuitry for the generation and application of stimulating signals. The output circuit allows a selection of stimulation signal amplitudes, provides a speed up in the charge rate of the output capacitor and imposes a rate limit on both itself and the elements generating the output initiate signals. However, it is to be understood that the concepts underlying the several aspects of the present invention need not be confined to a digital/analog combination or to the specific embodiment illustrated. It is therefore to be understood that, within the scope of the appended claims, the invention may be practiced otherwise than as specifically described.

We claim:

1. A body implantable stimulator which comprises means for alternatively and selectively providing a series of one of a predetermined plurality of independent output initiate signals and means providing stimulation signals in response to said output initiate signals including means for establishing the amplitude of said stimulation signals in accordance with the series of said output initiate signals that is provided.

2. A body implantable stimulator which comprises:
   power supply means providing an output potential and reference potential;
   a plurality of output terminal means for connection to the body;
   first means for applying a potential of opposite polarity to said output potential to at least one of said terminal means; and
   second means for selectively and alternatively applying one of a preselected plurality of potentials within the range from said reference potential to said output potential to at least one other of said terminal means, said first and second means acting simultaneously.

3. The stimulator of claim 2 further comprising means providing output initiate signals for establishing the potential applied to said other terminal means.

4. The stimulator of claim 2 further comprising means for providing first and second output initiate signals, said selectively applying means comprising first means responsive to said first initiate signals for applying a first predetermined potential to said other terminal means and second means responsive to said second initiate signals for applying a second predetermined potential to said other terminal means.

5. The stimulator of claim 4 wherein said first potential approximately equals said reference potential.

6. The stimulator of claim 5 wherein said second potential approximately equals said output potential.

7. The stimulator of claim 6 wherein said opposite polarity potential and said second potential have approximately the same absolute value.

8. A body implantable stimulator which comprises:
means for alternatively and selectively providing a series of first or second independent output initiate signals; and
means responsive to said output initiate signals for providing stimulation signals including first means responsive to said first initiate signals for providing a stimulation signal having a first predetermined energy level and second means responsive to said second initiate signals for providing a stimulation signal having a second predetermined energy level.

9. A body implantable stimulator which comprises means for alternatively and selectively providing a series of one of a predetermined plurality of independent output initiate signals and means providing stimulation signals in response to said output initiate signals including means for establishing the amplitude and duration of said stimulation signals in accordance with the series of said output initiate signals that is provided.

10. A body implantable stimulator which comprises means for alternatively and selectively providing a series of one of a predetermined plurality of independent output initiate signals and means providing stimulation signals in response to said output initiate signals including means for establishing the amplitude, duration and repetition rate of said stimulation signals in accordance with the series of said output initiate signals that is provided.

* * * * *